United States Patent
Fishler et al.

(10) Patent No.: US 9,659,508 B2
(45) Date of Patent: May 23, 2017

(54) MICROFLUIDIC PLATFORM AND METHODS FOR USING THE SAME

(71) Applicant: TECHNION RESEARCH & DEVELOPMENT FOUNDATION LIMITED, Haifa (IL)

(72) Inventors: Rami Fishler, Kiryat Motzkin (IL); Josue Sznitman, Haifa (IL)

(73) Assignee: Technion Research & Development Foundation Limited, Haifa (IL)

( * ) Notice: Subject to any disclaimer, the term of this patent is extended or adjusted under 35 U.S.C. 154(b) by 165 days.

(21) Appl. No.: 14/449,199

(22) Filed: Aug. 1, 2014

(65) Prior Publication Data
US 2015/0033872 A1    Feb. 5, 2015

Related U.S. Application Data

(60) Provisional application No. 61/860,993, filed on Aug. 1, 2013.

(51) Int. Cl.
*B01L 3/00* (2006.01)
*G09B 23/30* (2006.01)
*G01F 1/704* (2006.01)
*G01N 15/00* (2006.01)

(52) U.S. Cl.
CPC ............. *G09B 23/30* (2013.01); *G01F 1/704* (2013.01); *B01L 3/5027* (2013.01); *G01N 2015/0046* (2013.01)

(58) Field of Classification Search
CPC ........................................................ B01L 3/00

USPC ................................ 422/68.1, 502, 503, 504
See application file for complete search history.

(56) References Cited

U.S. PATENT DOCUMENTS

| | | | |
|---|---|---|---|
| 2002/0067992 A1* | 6/2002 | Bridger et al. ................. | 417/53 |
| 2002/0185184 A1* | 12/2002 | O'Connor et al. ........... | 137/822 |
| 2004/0238052 A1* | 12/2004 | Karp et al. .................... | 137/822 |
| 2005/0092662 A1* | 5/2005 | Gilbert et al. ................. | 210/97 |
| 2007/0026439 A1* | 2/2007 | Faulstich et al. ................ | 435/6 |
| 2008/0311585 A1* | 12/2008 | Gao et al. ........................ | 435/6 |
| 2009/0206293 A1* | 8/2009 | Beerling et al. .............. | 251/331 |

OTHER PUBLICATIONS

Sudhajer Chhabra, Ajay K. Prasad, Flow and Particle Dispersion in a Pulmonary Alveolus—Part I: Velocity Measurements and Convevtice Particle Transport, May 2010, vol. 132, pp. 051009-1-12.
Sudhajer Chhabra, Ajay K. Prasad, Flow and Particle Dispersion in a Pulmonary Alveolus—Part II: Effect of Gravity on Particle Transport, May 2010, vol. 132, pp. 051010-1-8.
F. F. Cinkotai, Fluid flow in a model alveolar sac, Aug. 1974, vol. 37, No. 2, pp. 249-251.

(Continued)

*Primary Examiner* — Brian J Sines
(74) *Attorney, Agent, or Firm* — Roach Brown McCarthy & Gruber, P.C.; Kevin D. McCarthy

(57) ABSTRACT

The present invention provides a microfluidic device which includes at least 3 chambers, a chamber inlet, at least 2 dichotomously branching generations of channels, a channel inlet, and a channel outlet, wherein the channels and the chambers are separated by deformable walls, wherein each wall is lined with at least one cavity, and wherein the cavity is fluidly connected to the channel.

20 Claims, 7 Drawing Sheets

(56) References Cited

OTHER PUBLICATIONS

Figure 1:
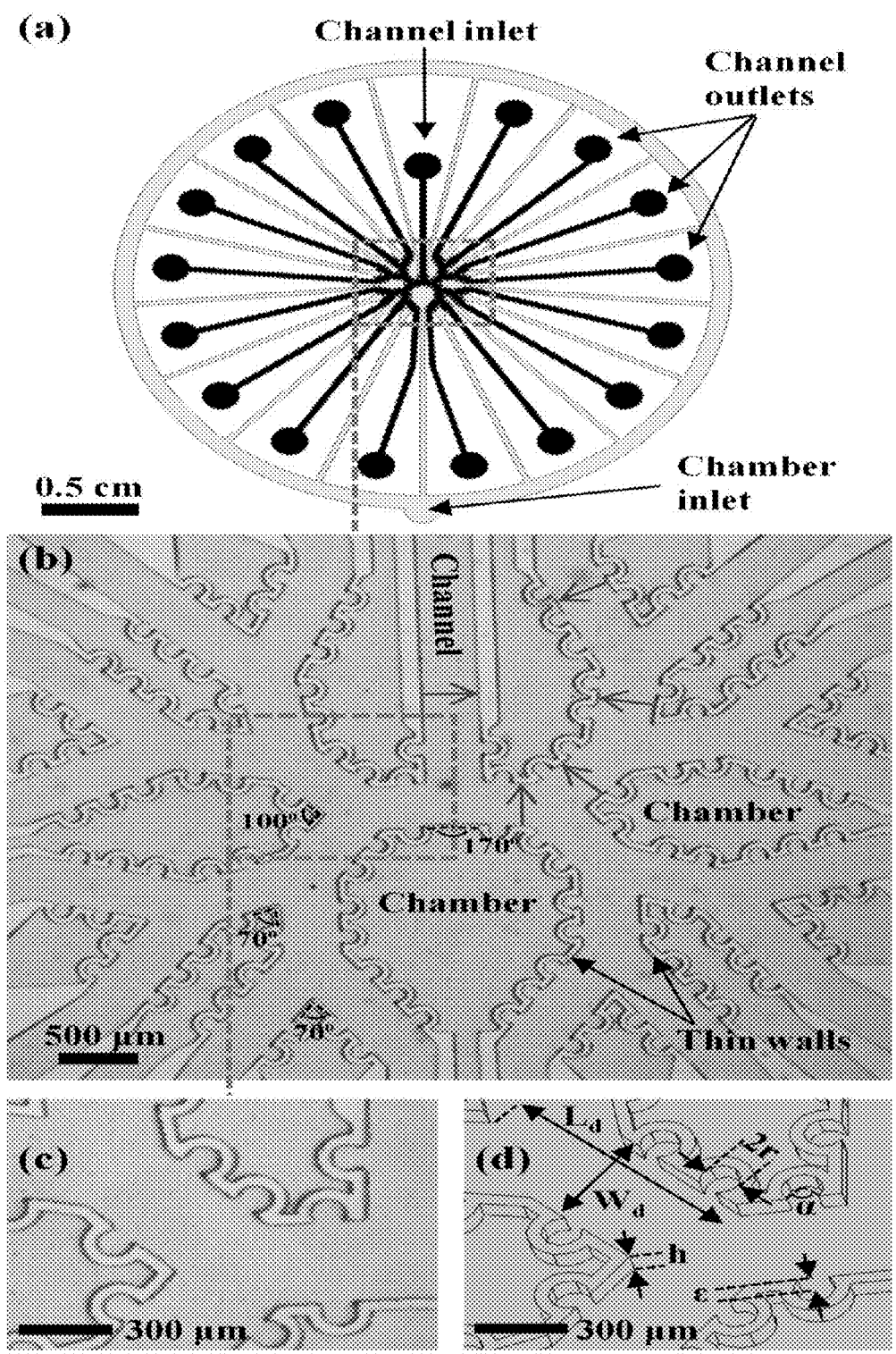

Rami Fishler, Molly K. Mulligan, Josué Sznitman, Acinus-on-a-chip: A microfluidic platform for pulmonary acinar flows, Aug. 31, 2013, pp. 2817-2823.
J. N. Galloway et al., Nitrogen cycles: past, present, and future, 2004, Biogeochemistry 70, pp. 153-226.
Josué Sznitman, Convective gas transport in the pulmonary acinus: Comparing roles of convective and diffusive lengths, 2009, pp. 789-792.
Josué Sznitman, Respiratory microflows in the pulmonary acinus, 2013, pp. 284-298.
Josué Sznitman, Thomas Heimsch, Respiratory Flow Phenomena and Gravitational Deposition in a Three-Dimensional Space-Filing Model of the Pulmonary Acinar Tree, Mar. 2009, vol. 131, pp. 031010-1-16.
A Tippe, A Tsuda, Recirculating Flow in an Expanding Alveolar Model: Experimental Evidence of Flow-Induced Mixing of Aerosols in the Pulmonary Acinus, 1999, vol. 31 No. 8, pp. 979-986.
Akira Tsuda et al., Chaotic mixing of alveolated duct flow in rhythmically expanding pulmonary acinus, 1995, pp. 1055-1063.
John Wright et. al., Robust Face Recognition via Sparse Representation, Feb. 2009, vol. 31 No. 2, pp. 210-227.

\* cited by examiner

FIGURE 10

MICROFLUIDIC PLATFORM AND METHODS FOR USING THE SAME

FIELD OF INVENTION

This invention is directed to; inter alia, a microfluidic device which includes at least 3 chambers, a chamber inlet, at least 2 dichotomously branching generations of channels, a channel inlet, and optionally a channel outlet.

BACKGROUND OF THE INVENTION

Through manipulating fluids using microfabricated channel and chamber structures, microfluidics is a powerful tool to realize high sensitive, high speed, high throughput, and low cost analysis. In addition, the method can establish a well-controlled microenvironment for manipulating fluids and particles. It also has rapid growing implementations in both sophisticated chemical/biological analysis and low-cost point-of-care assays. Some unique phenomena emerge at the micrometer scale. For example, reactions are completed in a shorter amount of time as the travel distances of mass and heat are relatively small; the flows are usually laminar; and the capillary effect becomes dominant owing to large surface-to-volume ratios. In the meantime, the surface properties of the device material are greatly amplified, which can lead to either unique functions or problems that would not be encountered at the macroscale. Also, each material inherently corresponds with specific microfabrication strategies and certain native properties of the device. Therefore, the material for making the device plays a dominating role in microfluidic technologies.

The ability to precisely forecast the fate of inhaled aerosols is necessary for the development of inhaled aerosolized drugs and assessing health threats of inhaled pollutant particles.

Until present, acinar flows have been commonly investigated using computational fluid dynamic (CFD) simulations and scaled-up experimental models based on hydrodynamic similarity matching. Computational approaches have considerably evolved over the past few decades: while examples of earlier acinar models comprised single alveoli or alveolated ducts, more recent models span across realistic acinar tree structures, featuring multiple generations of alveolated ducts. The growing body of numerical studies has suggested that a sequence of alveolar flow patterns co-exist along the acinar tree: the first proximal generations of the pulmonary acinar tree, characterized by a low ratio of alveolar to ductal flow rates (denoted as Qa/Qd), exhibit intricate recirculating flows inside the alveolus with irreversible fluid pathlines. In contrast, deeper acinar generations, where values of Qa/Qd gradually increase, exhibit more radial-like streamline configurations that yield quasi-reversible pathlines. In particular, simulations across multi-generation acinar trees agree with earlier predictions obtained using models of a single alveolus, when screening for values of the ratio Qa/Qd. Recently, direct lung imaging data of rat and mouse acini have led to the first CFD simulation of anatomically-based acinar flows. However, these studies have been limited to terminal alveolar sacs or a few alveoli surrounding a single duct. Yet, investigations of acinar flows are still largely driven by studies using generic alveolar geometries.

A number of experimental models incorporating a single alveolus or an alveolated duct have been reported (Chhabra and Prasad, 2011; Cinkotai, 1974; Karl et al., 2004; Tippe and Tsuda, 2000). In contrast to computational studies, however, experimental models of an acinar tree that also mimic expanding and contracting breathing motion have not been introduced so far. Such models remain critically needed both for validation of computational predictions and as investigative tools. To date, the scaled-up experiment with the largest number of acinar generations was introduced by Ma et al. (2009), featuring three acinar bifurcations lined with toroidal alveoli; however, the model was limited to studies under rigid wall conditions only. A more anatomically-realistic model was recently presented in a scaled-up silicone replica cast expanded by changes in pressure from the surrounding liquid in a closed chamber; however, the setup was limited to the last two generations of an acinar sac. In both instances, scaled-up experiments came short of capturing the hypothesized transition from recirculating to radial flows in the acinus, and thus did not confirm numerical predictions (Sznitman et al., 2009; Tsuda et al., 1995) of flow topologies hypothesized across pulmonary acinar trees. Another critical drawback with the use of scaled-up experiments lies in their limited ability to investigate particle transport and deposition due to the challenges in simultaneously matching the dimensionless numbers for flow and for particles.

SUMMARY OF THE INVENTION

In one embodiment, the present invention provides a microfluidic device comprising at least 3 chambers, a chamber inlet, at least 2 dichotomously branching generations of channels, a channel inlet, and optionally a channel outlet, wherein the channels and the chambers are separated by deformable walls, wherein each wall is lined with at least one cavity, wherein the cavity is fluidly connected to the channel. In one embodiment, the deformable walls define the chambers and the channels.

In one embodiment, the present invention further provides a device comprising a rigid capsule, a top layer, a bottom, layer, a liquid inlet, and a microfluidic arrangement, wherein the top layer, the bottom, layer, the liquid inlet, and the microfluidic arrangement are encapsulated within the rigid capsule, said microfluidic arrangement comprises at least 3 chambers, a chamber inlet, at least 2 dichotomously branching generations of channels, a channel inlet, and optionally a channel outlet, wherein the channels and the chambers are separated by deformable walls, wherein each wall is lined with at least one cavity, wherein the cavity is fluidly connected to the channel.

In one embodiment, the present invention provides a method for assessing the trajectory of a microparticle or a nanoparticle in a lung. In one embodiment, the present invention provides a method for assessing the trajectory of a microparticle or a nanoparticle, comprising the steps of: (a) labeling said microparticle or said nanoparticle; (b) obtaining a air suspension comprising a labeled microparticle or a labeled microparticle; (c) pumping said solution comprising a labeled microparticle or a labeled microparticle into the device of claim 1; and (d) characterizing particle trajectories or deposition sites using light or fluorescent microscopy; thereby, assessing the trajectories and/or deposition sites and/or overall deposition rate of a microparticles or a nanoparticles. In another embodiment, a microfluidic device or a device as described herein comprises: nanoparticles, microparticles or both.

BRIEF DESCRIPTION OF THE DRAWINGS

FIG. 1. Microfluidic device of the acinar tree network. (a) CAD drawing of one possible design of the present invention. (b,c) Close-up snapshots of the acinar tree structure showing the channels, the chambers, and the thin walls separating them. Purple arrows indicate the location and positive x-direction of the flow profiles presented in FIG. 3. (d) 3D CAD drawing illustrating the shape of the thin acinar walls.

Figure 2:
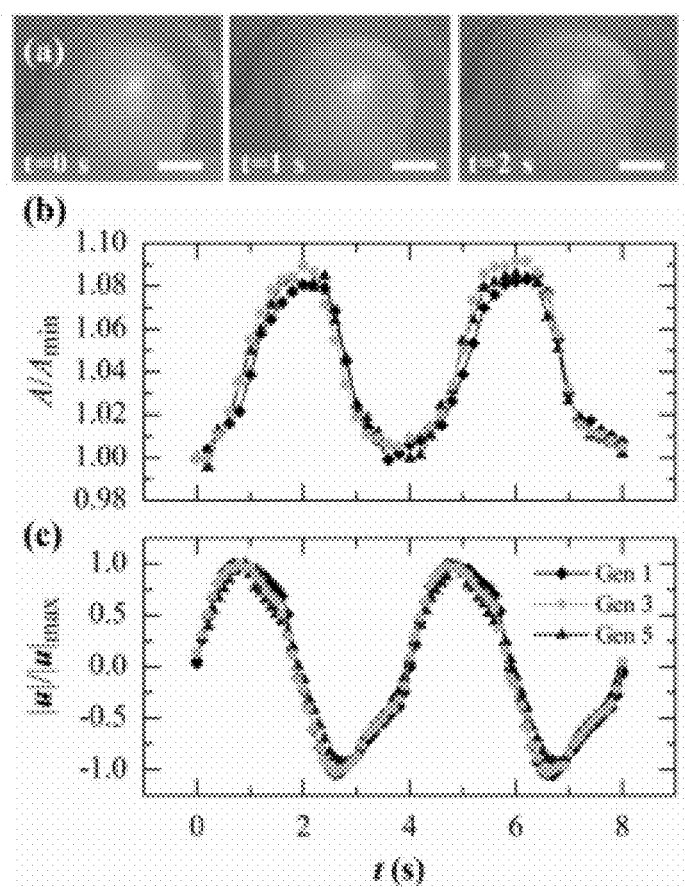

FIG. 2. (a) Time-lapse sequence of an alveolus located at generation 1, at minimum (t=0 s), intermediate (t=1 s) and maximum (t=2 s) expansion. Scalebar=50 μm. (b) Normalized cross-sectional area ($A/A_{min}$) measured at the midplane of the alveolus for generations 1, 3 and 5. (c) Normalized ductal streamwise velocity magnitude ($|u|/|u|_{max}$) for an ROI located near the opening of the alveolus for generations 1, 3 and 5, where corresponds here to the peak velocity magnitude measured for each generation, respectively.

Figure 3:
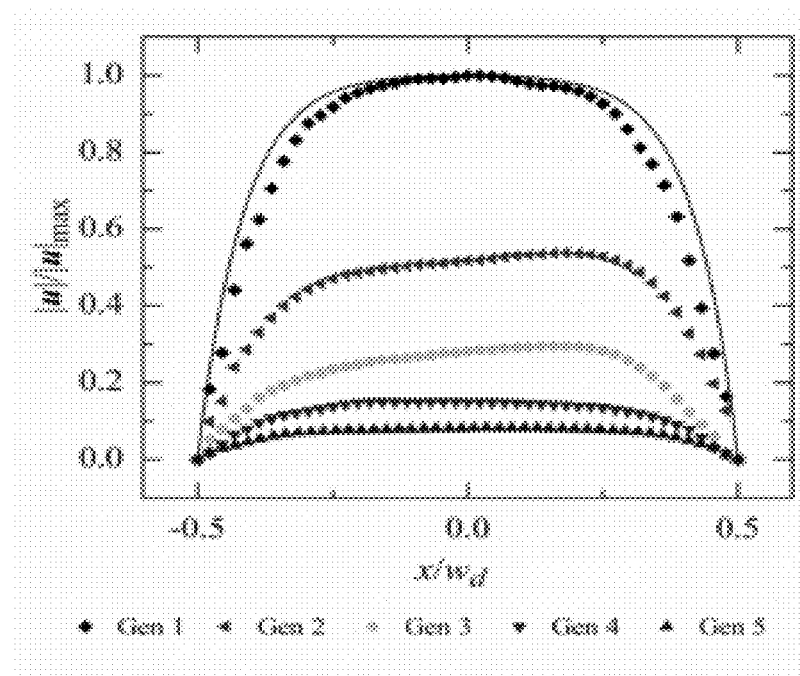

FIG. 3. Normalized ductal velocity profiles ($|u|/|u|_{max}$) extracted from PIV along the width of the channel for generations 1 through 5 at the locations illustrated in FIG. 1; x=0 coincides with the midpoint location across the channel and $|u|_{max}$=0.0104 m/s corresponds here to the peak velocity magnitude measured in generation 1. PIV measurements are shown here at peak inhalation (t/T=1/4) and the black line corresponds to the analytical velocity profile for creeping flow inside a rectangular channel with $w_d$=345 μm and h=88 μm.

Figure 4:
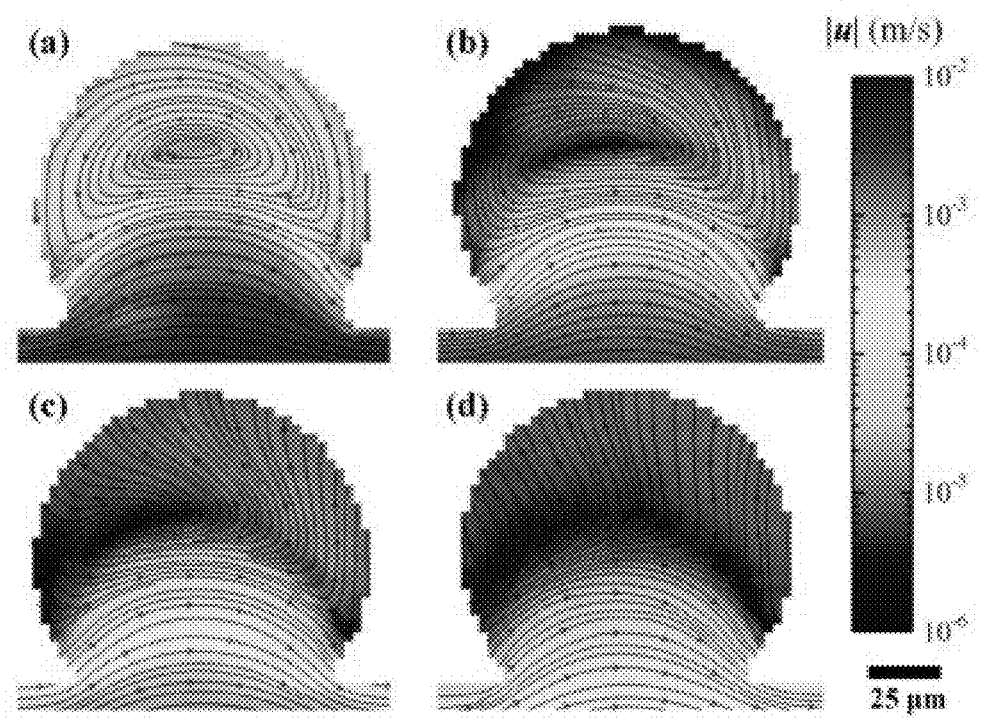

FIG. 4. Experimental velocity magnitudes and streamline patterns for a projection of the flow extracted from the midplane of an alveolus located at (a) generation 1, (b) generation 3, (c) generation 5, and (d) generation 5 using a reduced ductal flow rate. Flow fields are shown at approximately peak inhalation (t/T=1/4).

Figure 5:
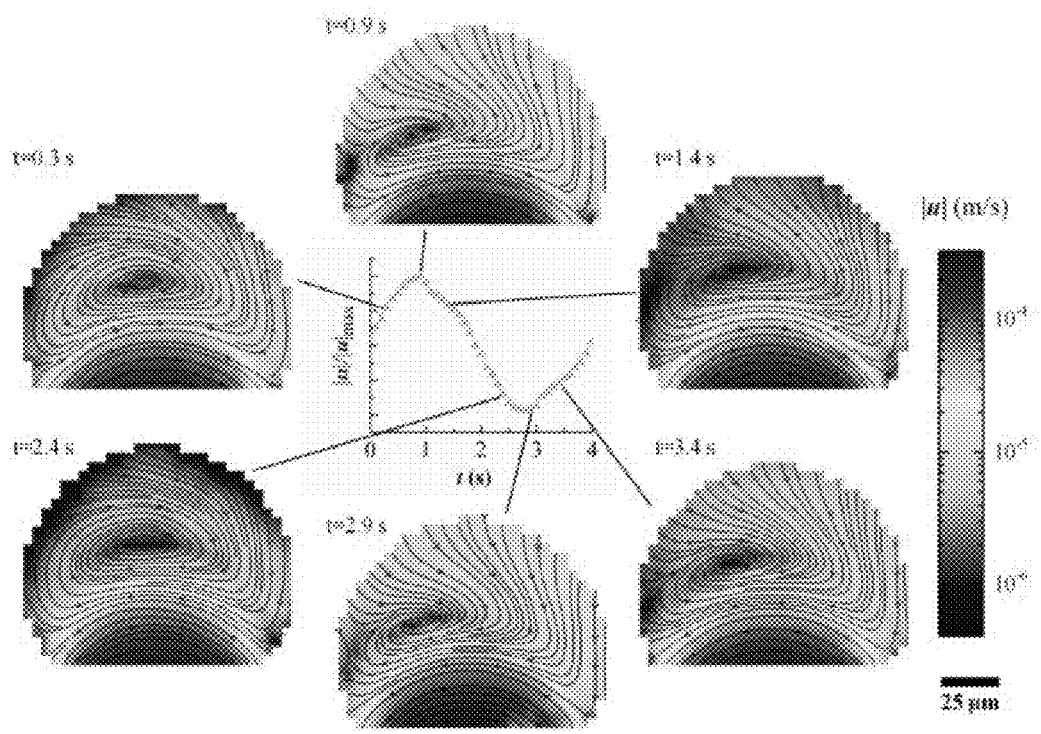

FIG. 5. Velocity magnitude and streamlines inside an alveolus located at generation 5. Data are shown for a projection of the flow at the midplane for several time instances along the breathing flow cycle.

Figure 6:
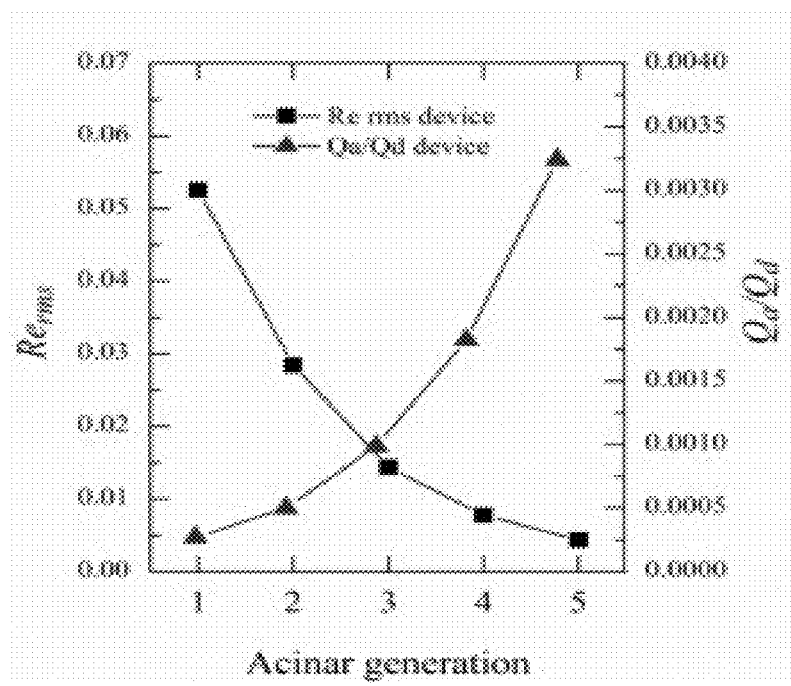

FIG. 6. Experimentally estimated values of the root-mean square Reynolds number ($Re_{rms}$) and the alveolar to ductal flow ratio ($Q_a/Q_d$) along device generations 1 to 5. Note that values of $Q_a/Q_d$ are presented at peak inspiration during the breathing cycle.

Figure 7:
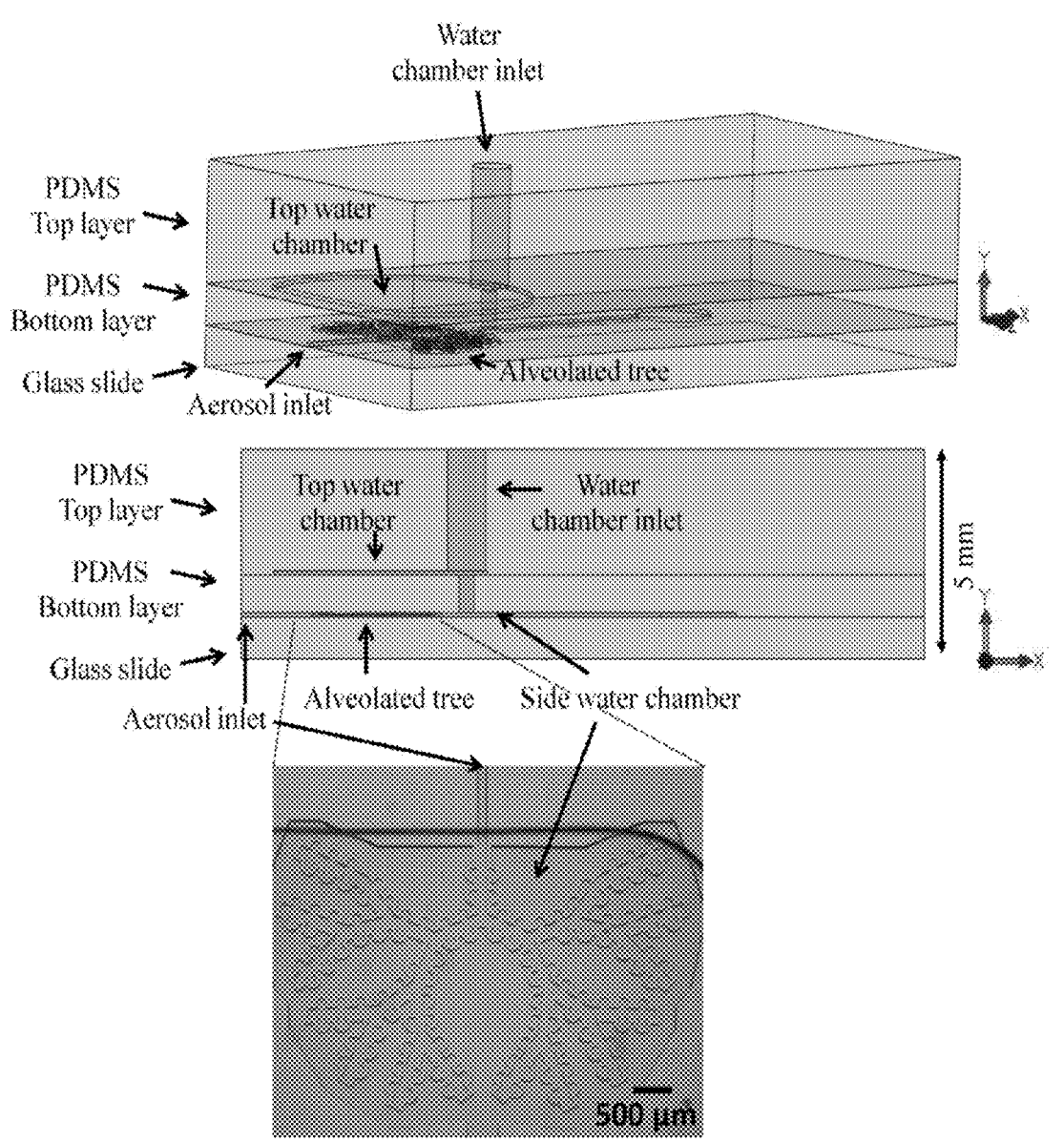

FIG. 7. Illustrates different views of a device comprising a microfluidic arrangement. In this device there are two PDMS layers on top of a glass substrate. While the air channels and side water chambers are located between the first PDMS layer and the glass slide, the top water chamber is located between the first and second PDMS layers. The side water chambers and top water chamber are both fed with water through the same inlet. This inlet is connected to a syringe pump that controls the pressure inside the chambers. Increasing and reducing the pressure inside the water chambers in a cyclic fashion deforms the side walls of the channels as well as the first PDMS layer to simulate airway wall motion inside the lungs, and thus recreate a physiologically-real breathing motion with the correct range of wall strains.

Figure 8:
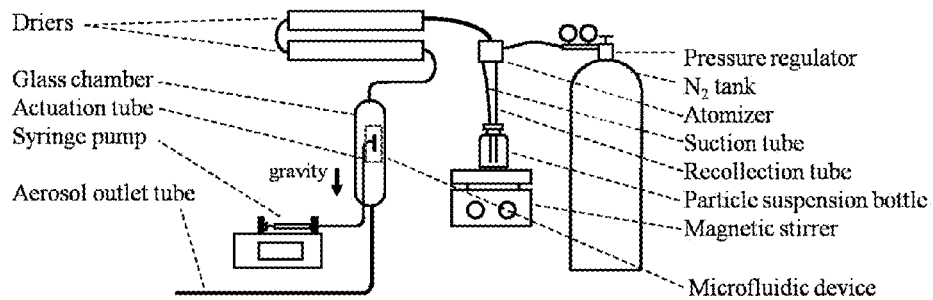

FIG. 8. Illustrates an aerosol exposure system exposing microfluidic device to aerosols of known composition and particle size. A water suspension of fluorescent polystyrene particles is connected to an atomizer (TSI aerosol generator 3076) with constant mixing. The resulting aerosol is passed through two diffusion dryers into a sealed glass chamber and leaves the chamber through an outlet tube. The microfluidic arrangement is located inside a custom-designed air-tight glass chamber with the leading channel parallel to the orientation of gravity, and exposure to particles occurs through actuation of the device walls leading to transport of airborne particle into and out of the device.

Figure 9:
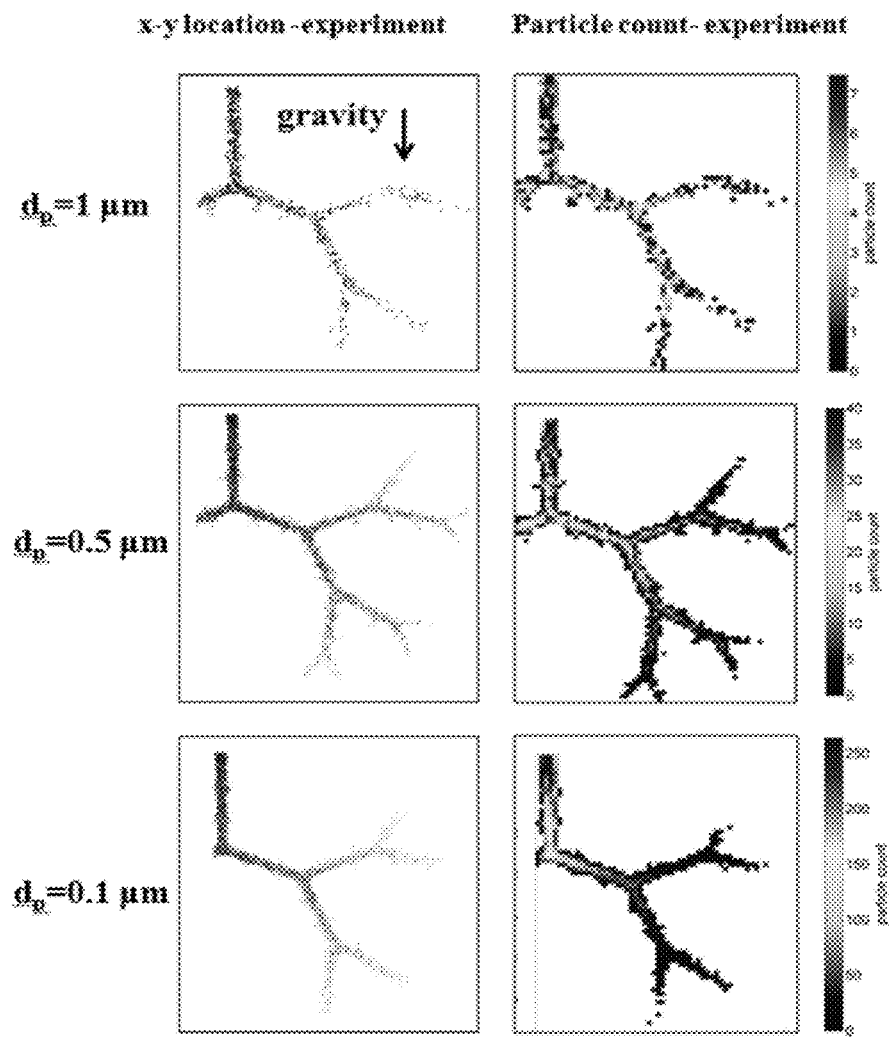

FIG. 9. Is a set of graphs showing the location of aerosolized particles of 3 different size groups within a device incorporating the microfluidic arrangement described herein.

Figure 10:
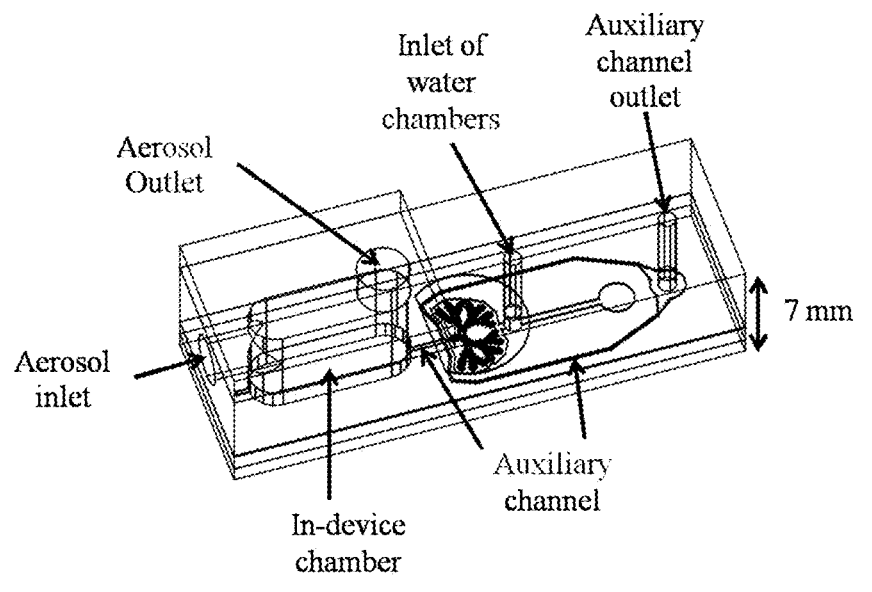

FIG. 10. Is a device which facilitates exposure to airborne particles without the use of a large exposure chamber. An in-device chamber is added to the device featuring an inlet and an outlet through which a steady stream of aerosol is driven.

DETAILED DESCRIPTION OF THE INVENTION

In one embodiment, the present invention provides a microfluidic device comprising at least 3 chambers, a chamber inlet, at least 2 dichotomously branching generations of channels, a channel inlet, and optionally a channel outlet, wherein the channels and the chambers are separated by deformable walls, wherein each wall is lined with at least one cavity, wherein the cavity is fluidly connected to the channel. In one embodiment, the present invention provides a microfluidic acinar device.

In one embodiment, the deformable walls are deformable alveolar walls. In one embodiment, the present invention provides that the cavity is cylindrical. In one embodiment, the present invention provides that the cavity is rectangular. In one embodiment, the present invention provides that the cavity is polyhedral. In some embodiments, the phrases "microfluidic device" and "microfluidic arrangement" are used interchangeably.

In another embodiment, a device of the invention comprises a box or a capsule encapsulating or carrying within a microfluidic arrangement, a top layer, a bottom layer, a liquid inlet or liquid inlet chamber, and optionally a pump. In one embodiment, the box or the capsule is made of: plastic, glass, or any other materials that are rigid. In one embodiment, the box or the capsule is made of a hydrophobic material.

In another embodiment, the top layer, the bottom layer or both comprises or composed of a polymeric organosilicon such as but not limited to Polydimethylsiloxane. In another embodiment, the top layer, the bottom layer or both are supported by a rigid layer such as glass.

In another embodiment, the top layer, the bottom layer or both are 0.1 mm to 20 mm thick. In another embodiment, the top layer, the bottom layer or both are 0.5 mm to 10 mm thick. In another embodiment, the top layer, the bottom layer or both are 1 mm to 10 mm thick. In another embodiment, the top layer, the bottom layer or both are 1 mm to 5 mm thick.

In another embodiment, the microfluidic arrangement is located between the top layer and the bottom layer. In another embodiment, the microfluidic arrangement is located between a rigid layer supporting the top layer (underneath the top layer) and the bottom layer. In another embodiment, the microfluidic arrangement comprises (from bottom to top) a bottom layer, the microfluidic and the top layer. In another embodiment, the microfluidic arrangement comprises (from bottom to top) the bottom layer, the microfluidic arrangement, and a rigid layer supporting the top layer. In another embodiment, the microfluidic arrangement comprises (from bottom to top) a first rigid layer supporting the bottom layer, the bottom layer, the microfluidic arrangement, and a second rigid layer supporting the top layer.

In another embodiment, a liquid/water chamber is located between the top and the bottom layers. In another embodiment, a liquid/water chamber is located between the rigid layer supporting the top layer and the bottom layer. In another embodiment, a liquid/water chamber is a top or central liquid/water chamber (see FIG. 1) and is located between the top and the bottom layers.

In another embodiment, side liquid/water chambers and top/central liquid/water chamber (see FIG. 1) are both fed with liquid (such as but not limited to: water) through one or more liquid inlets. In another embodiment, side liquid/water chambers and top/central liquid/water chamber (see FIG. 1) are both fed with liquid (such as but not limited to: water) through the same liquid inlet.

In another embodiment, the liquid inlet/s is/are connected/coupled to a pump that controls the pressure inside the chambers. In another embodiment, the liquid inlet/s is/are connected/coupled to a syringe pump that controls the pressure inside the chambers. In another embodiment, the liquid inlet is connected/coupled to a syringe pump that controls the pressure inside the central/top chamber. In another embodiment, the liquid inlet is connected/coupled to a syringe pump that controls the pressure inside the side chambers.

In another embodiment, the microfluidic arrangement comprises (from bottom to top) the capsule's base, the bottom layer, the microfluidic arrangement, a rigid layer supporting the top layer, and the capsule's top. In another embodiment, the microfluidic arrangement comprises (from bottom to top) the capsule's base, a first rigid layer supporting the bottom layer, the bottom layer, the microfluidic arrangement, a second rigid layer supporting the top layer, and the capsule's top.

In another embodiment, the channels are air channels. In another embodiment, the chambers are liquid chambers (such as water).

In another embodiment, increasing and reducing the pressure inside the liquid chambers (within the microfluidic arrangement) in a cyclic fashion deforms the side walls of the channels as well as the bottom layer thus simulating airway wall motion inside the lungs, and thus recreate a physiologically-real breathing motion with the correct range of wall strains.

In another embodiment, provided herein an aerosol exposure system (FIG. 8) comprising tank filled with a liquid suspension of particles is connected to an atomizer (such as TSI aerosol generator 3076) with constant mixing. In another embodiment, the resulting aerosol is passed through two diffusion dryers into a sealed glass chamber and leaves the chamber through an outlet tube. In another embodiment, a microfluidic arrangement is located inside a custom-designed air-tight glass chamber with the leading channel parallel to the orientation of gravity, and exposure to particles occurs through actuation of the device walls leading to transport of airborne particle into and out of the device.

In another embodiment, the cavity is fluidly connected to a channel. In another embodiment, the cavity comprises an opening. In another embodiment, the opening faces a channel. In another embodiment, the cavity has an open portion fluidly connected to a channel and a close portion defined by the deformable wall. In another embodiment, the cavity assumes a structure of a half circle. In another embodiment, the cavity is cylindrical. In another embodiment, the cavity is rectangular. In another embodiment, the cavity is polyhedral.

In another embodiment, each wall comprises at least one cavity. In another embodiment, each wall comprises a plurality of cavities. In another embodiment, each wall comprises at least 6 cavities.

In another embodiment, deformable walls are flexible. In another embodiment, deformable walls are inflatable. In another embodiment, gasses can penetrate into the deformable walls. In another embodiment, gasses can diffuse through the deformable walls. In another embodiment, gasses are air. In another embodiment, gasses comprise $C_{O2}$.

In another embodiment, a chamber is surrounded by a wall. In another embodiment, a chamber comprises a bulb shape. In another embodiment, a chamber comprises a chamber inlet. In another embodiment, at least one chamber comprises a chamber inlet. In another embodiment, at least one chamber is devoid of a chamber inlet. In another embodiment, the area between one chamber and another chamber is a channel. In another embodiment, the area between a first wall defining a first chamber and a second wall defining a second chamber is a channel. In another embodiment, a device as described herein comprises at least two types of chambers each having a different volume or area. In another embodiment, a chamber as described herein has a distal (base) end and a proximal end. In another embodiment, the distal end faces the perimeter of the device. In another embodiment, the proximal end faces the center of the device.

In another embodiment, a proximal end of at least one chamber comprises an obtuse angle. In another embodiment, a proximal end of at least one chamber comprises an obtuse angle smaller than 140 degrees. In another embodiment, a proximal end of at least one chamber comprises an obtuse angle smaller than 130 degrees. In another embodiment, a proximal end of at least one chamber comprises an obtuse angle smaller than 120 degrees. In another embodiment, a proximal end of at least one chamber comprises an obtuse angle smaller than 110 degrees. In another embodiment, a proximal end of at least one chamber has an angle of 100 degrees. In another embodiment, a proximal end of at least one chamber comprises an obtuse angle smaller than 220 degrees. In another embodiment, a proximal end of at least one chamber comprises an obtuse angle smaller than 200 degrees. In another embodiment, a proximal end of at least one chamber comprises an obtuse angle smaller than 190 degrees. In another embodiment, a proximal end of at least one chamber comprises an obtuse angle of 150 to 190 degrees. In another embodiment, a proximal end of at least one chamber comprises an obtuse angle of 170 degrees.

In another embodiment, at least one chamber is filled with a fluid. In another embodiment, all chambers are filled with a fluid. In another embodiment, fluid is water. In another embodiment, fluid is an aqueous solution. In another embodiment, fluid is a buffer. In another embodiment, fluid is oil. In another embodiment, fluid is a buffer. In another embodiment, fluid is a gas or a combination of gasses. In another embodiment, fluid is air.

In another embodiment, a device as described herein comprises at least one chamber inlet fluidly coupled to at least one chamber. In another embodiment, a device as described herein comprises at least one chamber outlet fluidly coupled to at least one chamber. In another embodiment, a device as described herein comprises at least one channel outlet fluidly coupled to at least one channel. In another embodiment, the chamber inlet is adapted to connect at least one chamber to a fluid. In another embodiment, the chamber inlet is adapted to connect at least one chamber to an external source of fluid. In another embodiment, the chamber outlet or the channel outlet is a fluid drainage outlet. In another embodiment, the external source comprises a pump coupled to the chamber inlet.

In another embodiment, a channel or the distance between two walls (each defining a chamber) is from 150 to 1000 micrometers wide. In another embodiment, a channel or the distance between two walls (each defining a chamber) is from 200 to 800 micrometers wide. In another embodiment, a channel or the distance between two walls (each defining a chamber) is from 400 to 1000 micrometers wide. In another embodiment, a channel or the distance between two walls (each defining a chamber) is from 400 to 600 micrometers wide. In another embodiment, a channel or the distance between two walls (each defining a chamber) is from 150 to 500 micrometers wide. In another embodiment, a channel or the distance between two walls (each defining a chamber) is from 350 to 550 micrometers wide.

In another embodiment, the channels are 300 micrometers to 1.5 millimeters long. In another embodiment, the channels are 300 micrometers to 600 micrometers long. In another embodiment, the channels are 500 micrometers to 800 micrometers long. In another embodiment, the channels are 500 micrometers to 1.5 millimeters long. In another embodiment, the channels are 600 micrometers to 1.2 millimeters long. In another embodiment, the channels are 800 micrometers to 1.2 millimeters long. In another embodiment, the channels are 1.0 millimeter to 1.2 millimeters long. In another embodiment, the channels are 1.2 millimeters to 1.5 millimeters long.

In another embodiment, a cylindrical cavity has a radius of 50 to 150 micrometers. In another embodiment, a cylindrical cavity has a radius of 50 to 80 micrometers. In another 15 embodiment, a cylindrical cavity has a radius of 80 to 100 micrometers. In another embodiment, a cylindrical cavity has a radius of 80 to 120 micrometers. In another embodiment, a cylindrical cavity has a radius of 100 to 150 micrometers.

In another embodiment, a rectangular cavity has a side size of 50 to 150 micrometers. In another embodiment, a rectangular cavity has a side size of 50 to 80 micrometers. In another 20 embodiment, a rectangular cavity has a side size of 80 to 100 micrometers. In another embodiment, a rectangular cavity has a side size of 80 to 120 micrometers. In another embodiment, a rectangular cavity has a side size of 100 to 150 micrometers.

In another embodiment, a polyhedral cavity has a width of 100 to 300 micrometers. In another embodiment, a polyhedral cavity has a width of 100 to 180 micrometers. In another embodiment, a polyhedral cavity has a width of 150 to 200 micrometers. In another embodiment, a polyhedral cavity has a width of 150 to 250 micrometers. In another embodiment, a polyhedral cavity has a width of 200 to 300 micrometers.

In another embodiment, a wall defining a chamber or walls of the invention is/are 15 to 80 micrometers thick. In another embodiment, a wall defining a chamber or walls of the invention 5 is/are 15 to 80 micrometers thick. In another embodiment, a wall defining a chamber or walls of the invention is/are 15 to 30 micrometers thick. In another embodiment, a wall defining a chamber or walls of the invention is/are 20 to 40 micrometers thick. In another embodiment, a wall defining a chamber or walls of the invention is/are 30 to 50 micrometers thick. In another embodiment, a wall defining a chamber or walls of the invention is/are 40 to 60 micrometers thick. In another embodiment, a wall defining a chamber or walls of the invention is/are 60 to 80 micrometers thick.

In another embodiment, a wall defining a chamber or walls of the invention is/are 40 to 800 micrometers high. In another embodiment, a wall defining a chamber or walls of the invention is/are 40 to 100 micrometers high. In another embodiment, a wall defining a chamber or walls of the invention is/are 50 to 250 micrometers high. In another embodiment, a wall defining a chamber or walls of the invention is/are 200 to 300 micrometers high. In another embodiment, a wall defining a chamber or walls of the invention is/are 250 to 400 micrometers high. In another embodiment, a wall defining a chamber or walls of the invention is/are 300 to 500 micrometers high. In another embodiment, a wall defining a chamber or walls of the invention is/are 400 to 600 micrometers high. In another embodiment, a wall defining a chamber or walls of the invention is/are 500 to 700 micrometers high. In another embodiment, a wall defining a chamber or walls of the invention is/are 600 to 800 micrometers high.

In another embodiment, the aspect ratio of said channels' height to width is 0.5 to 8. In another embodiment, the aspect ratio of said channels' height to width is 0.5 to 2. In another embodiment, the aspect ratio of said channels' height to width is 1 to 3. In another embodiment, the aspect ratio of said channels' height to width is 2 to 4. In another embodiment, the aspect ratio of said channels' height to width is 3 to 5. In another embodiment, the aspect ratio of said channels' height to width is 4 to 6. In another embodiment, the aspect ratio of said channels' height to width is 5 to 7. In another embodiment, the aspect ratio of said channels' height to width is 6 to 8.

In another embodiment, the distance between a channel edge and the center of said cylindrical cavity opening ($\epsilon$) is 20 to 140 micrometers. In another embodiment, the distance between a channel edge and the center of said cylindrical cavity opening ($\epsilon$) is 20 to 40 micrometers. In another embodiment, the distance between a channel edge and the center of said cylindrical cavity opening ($\epsilon$) is 30 to 60 micrometers. In another embodiment, the distance between a channel edge and the center of said cylindrical cavity opening ($\epsilon$) is 50 to 80 micrometers. In another embodiment, the distance between a channel edge and the center of said cylindrical cavity opening ($\epsilon$) is 70 to 120 micrometers. In another embodiment, the distance between a channel edge and the center of said cylindrical cavity opening ($\epsilon$) is 80 to 120 micrometers. In another embodiment, the distance between a channel edge and the center of said cylindrical cavity opening ($\epsilon$) is 100 to 140 micrometers.

In another embodiment, the cylindrical cavity opening has a half-angle of 20° to 40°. In another embodiment, the cylindrical cavity opening has a half-angle of 30° to 50°. In another embodiment, the cylindrical cavity opening has a half-angle of 40° to 50°. In another embodiment, the cylindrical cavity opening has a half-angle of 40° to 60°. In another embodiment, the cylindrical cavity opening has a half-angle of 50° to 75°. In another embodiment, the cylindrical cavity opening 20 has a half-angle of 60° to 80°.

In another embodiment, the device described herein comprises an elastomer. In another embodiment, the device described herein comprises plastic. In another embodiment, the device described herein comprises glass. In another embodiment, the device described herein comprises silicon. In another embodiment, the device described herein comprises polydymethylsiloxane. In another embodiment, the device described herein comprises perfluoropolymer. In another embodiment, the device described herein comprises an organosilicon compound. In another embodiment, the walls defining the chambers and the channels comprise a polymeric organosilicon compound. In another embodiment, the device described herein comprises a silicon-based organic polymer. In another embodiment, the device and/or the device's walls as described herein comprise a polymerized siloxane.

In another embodiment, organosilicon compound or polymerized siloxane is polydymethylsiloxane. In another embodiment, the device described herein is a polydymethylsiloxane microfluidic device. In another embodiment, the device described herein comprises a viscoelastic material. In another embodiment, the device described herein comprises an elastic solid. In another embodiment, the device described herein comprises a hydrophobic surface. In another embodiment, the device described herein comprises a hydropholic surface. In another embodiment, the device described herein comprises a material which does not allow aqueous solvents to infiltrate and swell the material. In another embodiment, the device described herein comprises a material which allows organic solvents to diffuse into the material.

In another embodiment, the device described herein provides a powerful microscale research platform. In another embodiment, the device described herein provides a powerful microscale research platform in the field of microfluidics (gasses and liquids) concerning the behavior, control, and manipulation of fluids on the microscale or nanoscale. In another embodiment, the device described herein provides specific dimensions to control the structure of the fluid flow and mimic portions of the mammalian airway system. In another embodiment, the device described herein provides pressure controls for the fluid to achieve specific flow rates which move the fluid through a microscale channel. In another embodiment, the device described herein provides a design with specific geometries that influence fluid mixing. In another embodiment, the term "fluids" is a sub-category of the phases of matter. In another embodiment, the term "fluids" encompasses liquids, or gases. In another embodiment, the term "fluids" are defined as a substance that will deform continuously under an applied stress.

In another embodiment, the device described herein provides at least one flow regime selected from: laminar, turbulent and creep. In another embodiment, the device described herein provides a combination of flow regimes. In another embodiment, the device described herein provides an anatomically-inspired acinar tree design (see FIG. 1).

In another embodiment, the device described herein comprises an acinar network of 2-8 dichotomously-branching generations of rectangular channels lined with cylindrical alveoli. In another embodiment, the device described herein comprises an acinar network of 4-6 dichotomously-branching generations of rectangular channels lined with cylindrical alveoli. In another embodiment, the device described herein comprises an acinar network of five dichotomously-branching generations of rectangular channels lined with cylindrical alveoli (black zones in FIG. 1a, areas marked as 'channel' in FIG. 1b). In another embodiment, thin (~20-80 μm) deformable walls (FIG. 1b-d) separate the channels and alveoli from the surrounding fluid or liquid-filled outer chambers (see gray zones in FIG. 1a, and areas marked as 'chamber' in FIG. 1b).

In another embodiment, alveoli and ductal walls are inflated and deflated in a cyclic fashion by altering liquid pressure inside the chambers. In another embodiment, the inlet flow rate into the device and the pressure inside the liquid/water chambers were controlled using two synchronized syringe pumps programmed to mimic a quiet tidal breathing scenario (T=3-6 s). In another embodiment, the pumps using provide linearly ramped flow rate. In another embodiment, only pressure inside liquid/water chambers was controlled, while the inlet flow rate into the device was defined by the instantaneous rate of change in the volume of the channels.

In another embodiment, acinar ducts measurements are in agreement with average morphometric acinar measurements (Haefeli&Bleuer and Weibel, 1988). In another embodiment, splitting angles of 30°-180° were chosen.

In another embodiment, the device of the invention comprises a recirculating zone or multi-vortex flow structures. In another embodiment, $\epsilon$ value that promotes single vortex formation according to the invention is $\epsilon$=51.1±8 μm such that r/h~0.5 to 0.8 and $\epsilon$/r~0.6 to 1.2. In another embodiment, the effective alveolar opening half-angle yields $\alpha$=42°±8° (see FIG. 2a).

In another embodiment, the device of the invention comprises a polymeric organosilicon. In another embodiment, the device of the invention is made by standard soft-lithography technique of Polydimethylsiloxane-based (PDMS), combined with a modified method for master production using deep reactive ion etching (DRIE) of a silicon on insulator (SOI) wafer. In another embodiment, the present alveolar cavities yield intricate 3D flow structures, even in the absence of wall motion.

In another embodiment, the device of the invention is made by fabricating a mask. In another embodiment, once the mask is fabricated as a master mold and is made from a silicon wafer and a negative photoresist. In another embodiment, a wafer is used as a flat surface to act as a substrate for the photoresist. In another embodiment, the photoresist is spun on and exposed in the areas desired to create a positive pattern of the microfluidic channels.

In another embodiment, the device of the invention is made by using a mask to expose the photoresist to light and create the master mold. In another embodiment, the photoresist to is exposed to light, hardened and crosslinked. In another embodiment, microchannels are laid down on the silicon wafer for creating the microfluidic device.

In another embodiment, PDMS is cast onto the master mold, where it takes on the negative 20 image of the master mold. In another embodiment, this gives the first three walls of the microfluidic device. In another embodiment, photolithography technique is used to create the master mold that is used to cast the PDMS.

In another embodiment, Micro-PIV is used for quantitative flow visualization inside the microfluidic device. In another embodiment, the device provides kinematic viscosity as air at ~24° c. (vair=1.55×10-5 m2/s, vglycerol/water mixture=1.51×10-5 m2/s).

In another embodiment, phase-locked, double-frame images of the particle-seeded flow are obtained using a commercial micro-particle image velocimetry (μPIV) system comprising of a low-speed camera, a double pulsed Nd-YAG laser, and a custom inverted microscope. In another embodiment, flows inside alveoli are characterized using particles smaller than 1.5 μm, while flows inside the acinar ducts were visualized using 4-0.2 μm particles.

In another embodiment, wall motion and fluid flow inside the device is controlled in a synchronized manner. In another embodiment, the outlets are sealed and the inlet is open to the environment rather then connected to a syringe pump. In another embodiment, fluid motion (either air or a glycerol solution) inside the device is driven by a cyclic motion of the walls similarly to the natural breathing mechanism. In another embodiment, it is also necessary to deform the ceiling of the device by, e.g., controlling the pressure in a chamber that lies on top of the channel.

In another embodiment, the present invention provides a method for assessing deposition levels of air-borne particulate matter (such as in inhaled aerosolized drugs) in the pulmonary acinus. In another embodiment, the present invention provides a method for assessing deposition levels of air-borne particulate matter comprising pumping a sample fluid into the a microfluidic device of the invention. In another embodiment, the method of the present invention makes use of altering water pressure inside the chambers (using e.g. a syringe pump). In another embodiment, alveoli and ductal walls are inflated and deflated in a cyclic fashion. In another embodiment, the present invention provides two different methods for controlling air-flow into the device: The first method is direct control of air flow rate into the inlet of the acinar tree and the second is by controlling the motion of the device walls (and optionally, the ceiling of the device) which in turn cause air motion.

In another embodiment, the present invention provides a method for assessing in-vitro deposition patterns of inhaled aerosols. In another embodiment, the present invention provides a method for assessing in-vitro deposition patterns of inhaled drug aerosols.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Methods

Anatomically-Inspired Acinar Tree Design

FIG. 1 shows computer-aided designs (CAD) alongside microscope snapshots of the microfluidic device used in this study. The acinar network model is constructed of five dichotomously-branching generations of rectangular channels lined with cylindrical alveoli (see black zones in FIG. 1a, and areas marked as 'channel' in FIG. 1b). These generations are designated as device generation 1 to 5, spanning the most proximal to distal generations. Thin (~45 µm) deformable walls (FIG. 1b-d) separate the channels and alveoli from the surrounding water-filled outer chambers (see gray zones in FIG. 1a, and areas marked as 'chamber' in FIG. 1b). By altering water pressure inside the chambers, alveoli and ductal walls are inflated and deflated in a cyclic fashion (see µPIV experiments in section 0 and Supplementary Movie S1 and S2). The inlet flow rate into the device and the pressure inside the liquid/water chambers were controlled using two synchronized syringe pumps programmed to mimic a quiet tidal breathing scenario (T=4 s) using linearly ramped flow rates; see Supplementary Material for details on device filling and actuation.

All acinar ducts are $w_d$=345±2 µm wide and $L_d$=762±2 µm long, in agreement with average morphometric acinar measurements (Haefeli&Bleuer and Weibel, 1988). To allow maximal use of the planar space, splitting angles of 170° (first bifurcation), 100° (second bifurcation), and 70° (two last bifurcations) were chosen, respectively. The radius of the cavities is r=58.1±0.1 µm, and the height of the channels and cavities is h=88.0±0.4 µm. Although microfluidic alveoli are slightly smaller compared to previous numerical models, this design choice allows to fit more alveoli along each duct, given the microfabrication design constraints (see details below). In addition, a relatively low aspect ratio of the channel width to height is used (i.e., $w_d/h \approx 3.9$), due to difficulties in fabricating high-aspect ratio walls.

It was shown that flows inside rigid-wall cylindrical micro-cavities may yield a range of flow topologies, including attached flow, a single recirculating zone or multi-vortex flow structures, depending on specific dimensionless geometrical parameters (i.e., r/h and ϵ/r, where ϵ is the distance between the channel edge and the cavity center). Since in the absence of wall motion alveolar models typically predict a single vortex inside the alveolar cavity. Thus a value of ϵ that promotes single vortex formation was chosen; namely, ϵ=51.1±0.5 µm such that r/h~0.66 and ϵ/r~0.88. Due to the finite radius of curvature of the sharp corner between the alveolus and the duct ($r_{curv}$=6.6±0.6 µm), the effective alveolar opening half-angle yields α=42°±1° (see FIG. 2a); this 15 value is reasonably close to the one found in a number of simulated alveolar configurations.

A standard soft-lithography technique was adopted for microfabrication of polydymethylsiloxane-based (PDMS) microfluidic devices, combined with a modified method for master production using deep reactive ion etching (DRIE) of a silicon on insulator (SOI) wafer (Pihl et al., 2005). Since such microfabrication techniques are generally limited to constructing 3D patterns that feature an extrusion of a 2D geometry (with a constant z height), our platform is currently restricted to planar geometries where all ducts and alveoli share the same height and lie within a single plane. Nevertheless, the quasi-3D geometry should not be confused with 2D flow configurations, where no out-of-plane flows exist. Indeed, the present alveolar cavities yield intricate 3D flow structures, even in the absence of wall motion. However, given the imaging limitations of our micro-PIV setup (see below).

Alternatively or in addition to a standard soft-lithography microfabrication technique for polydymethylsiloxane-based (PDMS) microfluidic devices was adopted[1], with a modified method of master production using deep reactive ion etching (DRIE) of a silicon on insulator (SOI) wafer[2]. This method is preferable for our specific purposes to epoxy-based negative photoresist (SU-8) photolithography since it allows better cleaning and easier re-use of the master given the high aspect ratio trenches (45 µm width to 88 µm height) that are necessary for casting the thin deformable PDMS walls. For the master fabrication, a 4" SOI double-side polished wafer with a device layer thickness of 135 µm, a buried oxide layer of 0.3 µm and a handle layer of 500 µm (Siltronix) was thermally oxidized to a thickness of 650 nm. The wafer was coated with an AZ® nLoF 2070 negative tone photoresist to a thickness of approximately 6 µm, pre-exposure baked at 110° c. for 5 min, and exposed to UV light using an MA6 mask aligner (Karl Suss) for a dose of 43 mj·cm$^{-2}$ through a transparency mask (CAD/Art Services). Post exposure, the wafer was baked at 110° c. for 3 min and developed in TMAH 2.5% for 90 s. The oxide layer was then removed from the areas of the wafer that were not covered by photoresist using buffered oxide etch. DRIE etching was performed using cycles of etching with an $SF_6$/Ar gas mixture and surface passivation using $C_4H_8$/Ar until the buried oxide layer was reached. During this step, the device layer was reduced to 88 µm since the top oxide layer and photoresist were completely removed during the etch. Finally, the master was cleaned using $O_2$ plasma (150 mW, 5 min) and silanized by exposing it to a Trichloro(1H,1H,2H,2H-perfluorooctyl)silane vapor in a vacuum desiccator for 12 h.

Device Filling and Actuation

Before filling the channels with the glycerol solution, the outer chambers (FIG. 1) were filled with water by covering the chamber inlet with a drop of DI water and placing the device in a desecrator under vacuum for <5 minutes. Remaining air inside the chambers was removed by connecting a water-filled syringe to the chamber inlet through a tube and applying pressure to the plunger until the air leaked through the air-permeable PDMS walls. The syringe was then connected to a syringe pump (PHD Ultra, Harvard apparatus) pre-programmed to mimic a quiet tidal breathing cycle (T=4 s) constructed of linear ramps, i.e., from zero to 900 μl/min in 1 sec, from 900 μl/min to −900 μl/min in 2 seconds and from −900 μl/min back to zero in 1 sec. The defined cycle caused a change in water pressure inside the chambers leading to breathing-like wall-expansion cycles of the thin PDMS walls (i.e., ducts and alveoli).

The glycerol solution was fed from the channel inlet (FIG. 1a) using a second syringe pump, programmed to repeat a flow cycle with linearly ramped flow rates from zero to −150 μl/min to 150 μl/min and back to zero. Note that the programmed flow rates are not identical to the actual flow rates in the device as measured from PIV (see Results section). Thus, the pump programs were empirically selected in order to mimic physiologically-relevant wall displacements and Reynolds numbers. All outlets were open to a single reservoir placed on top of the device thus assuring unvarying pressure across all outlets and therefore a symmetric distribution of ductal flows. This reservoir was made by attaching a PDMS slab to the top of the device, where a channel was carved out to allow collecting reserve fluid. To achieve exact time matching of the flow cycle and wall-expansion cycle (see FIG. 2 and Supplementary Movie S1 and S2), the two pumps were connected via the built-in 15-pin D-sub connector and the programs were initiated simultaneously by sending an I/O trigger command between the two pumps.

Micro-PIV Experiments

Micro-PIV was used for quantitative flow visualization inside the microfluidic device by seeding monodisperse 0.84 μm or 2 μm red fluorescent polystyrene latex (PSL) spherical particles (Fluoro-Max, Thermo Scientific) in a 64/36 (v/v) glycerol/water mixture. Given that the microfluidic device carries anatomically-realistic acinar length scales and that the working fluid has approximately the same kinematic viscosity as air at ~24° c. ($v_{air}$=1.55×10$^{-5}$ m$^2$/s, $v_{glycerol/water\ mixture}$=1.51×10$^{-5}$ m$^2$/s), both the Reynolds and Womersley numbers match closely those of air flowing within in vivo acinar networks (see Results and Discussion section below).

Phase-locked, double-frame images of the particle-seeded flow were obtained using a commercial micro-particle image velocimetry (μPIV) system (Flow Master MITAS, LaVision GmbH) consisting of a low-speed CMOS camera (1600× 1200 pixels), a double pulsed Nd-YAG laser (wavelength: 532 nm, output energy: 400 mJ, pulse duration: 4 ns), and a custom inverted microscope. Flows inside alveoli were characterized using 0.86 μm particles and a 20× objective, while flows inside the acinar ducts were visualized using 2 μm particles and a 10× objective. Note that experimental PIV data are depth-averaged over an effective depth of correlation of ~34 μm for measurements inside the duct and ~16 μm inside alveoli, using a standard analytical solution. Typically, a total of 500 image pairs were acquired at 10 Hz from which thirteen pairs corresponding to a specific (phase-locked) time instant in the breathing cycle (t/T) were extracted. These image pairs were analyzed using a sum-of-correlation algorithm (Meinhart et al., 2000). Since local flow velocities inside a single cavity are known to span across three orders of magnitude (see FIGS. 4 and 5), it was necessary to repeat measurements with varying time intervals between the double frames (i.e., 100 μs to 0.1 s), in an effort to resolve different flow regions inside the cavity. To reconstruct a complete and high-detailed map of flow patterns in individual alveoli, PIV results were patched into a single flow field by averaging overlapping data points.

For the analysis of velocities and wall expansion rates within alveoli (FIG. 2), a set of double-frame images was collected using simultaneously pulsed-laser and white light illumination. Despite lower contrast of the particles compared to pulsed-laser illumination alone, this setup enabled us to analyze the shape of the alveolus and alveolar velocities simultaneously as a function of time and assess the degree of synchrony between velocity and expansion cycles.

Example 1

Cyclic Flow Rates and Wall Motion

FIG. 2a shows a typical time-lapse sequence of an alveolus located at device generation 1 at minimum, intermediate and maximum expansion (from left to right), respectively. From such image analysis, the cross-sectional areas of alveoli were measured and plotted as a function of time 5 for generations 1, 3 and 5 (FIG. 2b), respectively. The cross-sectional area varies in a sinusoidal-like fashion with a change in area of ~8% compared to the minimal area ($A_{max}/A_{min}$≈1.08, where $A_{max}$ and $A_{min}$ are maximal and minimal cross-sectional areas, respectively). A self-similar expansion of the microfluidic alveolar geometry, would be expected to have maximal to minimal volume ratio would yield $V_{max}/V_{min}=(A_{max}/A_{min})^{3/2}$≈1.12. This value is slightly smaller than the expected volume ratio for tidal breathing (usually in the range between 1.167 and 1.25), but nevertheless lies within physiologically-relevant conditions. It should be emphasized, however, that geometrical expansions/contractions in our microfluidic model are not self-similar (i.e., r/h and ϵ/r change during the entire flow cycle) and the above analysis is only intended as a crude comparison of our experimental model with numerical studies that rely on self-similar kinematic wall displacement functions.

The time-dependent normalized velocity magnitude inside the alveolus was extracted from PIV obtained across a rectangular region of interest (ROI) located near the opening of the alveolus (FIG. 2c). It was observed that time-velocity curves are similar to measured curves obtained from spirometry (Berg et al., 2010), and wall motion is well synchronized with the fluid velocity (compare FIG. 2b and FIG. 2c). Minimum flow velocity coincides with minimum and maximum alveolus area, while the maximal velocity coincides with maximal expansion rate. In contrast to models where the flow is induced as a result of wall motion, however, the measured flow velocity is not exactly proportional to the rate of expansion throughout the flow cycle (see discussion in section Error! Reference source not found.).

Example 2

Ductal Flow Profiles

FIG. 3 shows profiles of the normalized streamwise velocity magnitude ($|u|/|u|_{max}$) along the width of the acinar ducts, extracted at the mid-height of the channel; results are presented at the instance of maximal inflow velocity for device generations 1 through 5. The locations from which the flow profiles were extracted (and the corresponding positive x-axis direction) are indicated by the purple arrows in FIG. 1b. For generation 1, the experimental velocity profile fits well with the analytic solution for creeping flow at the mid-height of a rectangular channel (FIG. 3). Note that here the use microfluidic channels with a relatively low aspect ratio (i.e., $w_d/h \approx 3.9$), is described, such that velocity profiles exhibit more plug-like characteristics compared to parabolic profiles in circular channels. In contrast to the nearly symmetric flow profile observed in generation 1, generations 2 and 3 are characterized by more asymmetric profiles; this result may be due to the proximity of the measurement location to the upstream bifurcation. However, the observed asymmetry is gradually reduced in the distal acinar generations of the model, as the local flow rate magnitude is reduced. Overall, velocity magnitudes decrease by approximately a factor of two at each bifurcation (FIG. 3), as anticipated following the dichotomous branching nature of the microfluidic acinar model.

Example 3

Alveolar Flow Patterns

Measured velocity magnitudes and streamline patterns inside alveoli are shown in FIG. 4. The data correspond to the projection of the flow along the midplane of the geometry (see micro-PIV methods) at the instance of maximal inflow velocity; FIGS. 4a,b and c correspond to acinar generations 1, 3 and 5, respectively. A gradual decrease in the ductal velocities passing near each alveolar opening is observed along the acinar tree, while local alveolar flow magnitudes decay across several orders of magnitude, as previously reported from simulations (Kumar et al., 2009; Sznitman, 2013; Sznitman et al., 2009). Moreover, a pronounced change was observed in flow patterns as a function of acinar generation, as numerically predicted: while in generation 1 the recirculation zone is centred close to the center of the alveolus and streamlines show a more closed configuration (FIG. 4a), in generation 5 the recirculation zone is centred at the proximal side of the alveolus and streamlines are more open (FIG. 4c). FIG. 4d shows velocity magnitudes and streamline patterns for generation 5 using a reduced ductal flow rate. Namely, the syringe pump 5 controlling the fluid flow at the inlet of the microfluidic device was stalled and flow was effectively driven by wall motion only. Under such conditions, flow recirculation disappears entirely from the alveoli located at generation 5, and only radial streamlines are seen to fill the alveolar cavity. To the best of our knowledge, this is the first time that experiments featuring cyclic wall motion reveal the existence of a wide range of alveolar flow patterns coexisting along the acinar tree, with a transition from closed to open streamline configurations with acinar depth, as previously suggested in numerical studies.

Up to this point, only flow patterns at the instant of maximal velocity were considered. To show how these patterns change with time, the alveolar flow field (i.e., velocity magnitudes and streamlines) was extracted, at several time instances during the flow cycle in a given alveolus located at generation 5 (FIG. 5). Numerical studies have shown that for self-similar expanding and contracting motion, a quasi-steady flow pattern is observed inside the alveolus where only flow magnitude is altered, and flow patterns remain virtually unchanged throughout the flow cycle. This behaviour follows mainly from the low Womersley (and Reynolds) numbers and the similarity of the instantaneous boundary conditions at different times during the cycle. A different way of understanding the self-similarity of the flow is to recognize that the nature of alveolar flows is determined by the ratio of alveolar to ductal flow rates ($Q_a/Q_d$). For an alveolus with self-similar deformations, the ratio $Q_a/Q_d$ remains constant throughout the cycle and flow patterns thus remain unchanged. In the present work, however, expansion is not self-similar since $\epsilon/r$ and $r/h$ are not constant during the expansion/contraction cycle, but rather a function of time. In addition, there is a small degree of temporal asynchrony between wall motion and flow (FIG. 2). As a result, the value of $Q_a/Q_d$ varies throughout the flow cycle causing shifts in the instantaneous vortex location. Nevertheless, this type of mismatch between velocity and expansion rate may occur in vivo as a result of a small, yet significant geometrical hysteresis known to exist during tidal breathing.

FIG. 6 shows experimental values of $Q_a/Q_d$ at peak velocity for generations 1 through 5. Due to the planar nature of our measurements (i.e., PIV and direct microscopy imaging), this ratio is estimated from $Q_d = |u|_{avg} \times w_d \times h$, where $|u|_{avg}$ is the average velocity (obtained from PIV) in the duct's midplane, and $Q_a = (dA/dt) \times h$, where A is the cross-sectional area in the midplane of the alveolus, as calculated from image analysis (see FIG. 3). Experimental values of $Q_a/Q_d$ in our microfluidic model are in good agreement with the broad range of anticipated values of $Q_a/Q_d$ in acinar generations 0 to 4. In particular, these values are consistent with the observed transition from nearly-closed recirculating streamlines in generation 1 (FIG. 4a) to more open, radial-like streamline configurations in generation 5 (FIG. 4c). It should be noted, however, that the above discussion regards only the value $Q_a/Q_d$ at maximal flow velocity, while instantaneous values of $Q_a/Q_d$ change over time. In addition, at maximal strain, the alveolar walls bend such that the cross-sectional area does not remain constant across the channel height in the z direction.

Example 4

Womersley and Reynolds Numbers

To further assess the physiological relevance of our microfluidic model, the corresponding Womersley and Reynolds numbers inside the alveolar ducts were calculated. The Womersley number is defined as $Wo = D_h (2\pi f/\nu)^{1/2}$, where $D_h = 141.4$ μm is the hydraulic diameter of the duct and $f = 1/T$ is the breathing frequency. Here, the Womersley number is constant with a value of ~0.045 for all device generations and during the entire expansion cycle, since all generations share the same hydraulic diameter and changes in the width of the channel during the expansion cycle are small compared to the channel width (<5%). The low value of Wo estimated is in line with predicted values from semi-empirical models and indicates that unsteady acceleration is small compared to viscous effects. This conclusion implies that changes observed in the flow patterns inside alveolar cavities over the breathing cycle (FIG. 5) are not due to unsteady effects but correspond rather to flow field solutions in the creeping regime under time-dependent boundary conditions.

Finally, for each acinar generation the corresponding root-mean-square (RMS) Reynolds number, $Re_{rms} = \bar{U}_{max}/D_h/(\nu_{glycerol\ solution} \sqrt{2})$, was assessed, where $\bar{U}_{max}$ is taken as the average velocity across the duct midplane at the instant of maximal flow rate. Here, an ideal sinusoidal velocity curve versus time (see FIG. 3) was assumed. Analysis of time-dependent velocities at the opening of the alveolus (FIG. 3) shows that with this approximation, the calculated $Re_{rms}$ is within 5% of the true $Re_{rms}$ calculated using the entire sequence of measured velocities. Our estimated values of $Re_{rms}$ (FIG. 6) correspond to values anticipated in acinar generations 4 to 8, according to semi-empirical models (Sznitman, 2013; Akira Tsuda et al., 2008). Note that while values of $Q_d/Q_a$ in our experiments correspond to the more proximal generations of the acinus, $Re_{rms}$ (and hence flow velocities) seem to align better with those estimated in the more distal regions of the acinus. It should be emphasized, however, that the semi-empirical values of both $Re_{rms}$ and $Q_d/Q_a$ are derived from geometrical models built using average measurements in lung casts and were never measured in vivo. Moreover, given the versatility of our microfluidic setup, higher flow rates can be experimentally used in conjunction with higher expansion and contraction rates to reconcile the discrepancy. Overall, our microfluidic acinar platform captures physiologically-relevant hydrodynamic features of acinar flows.

Thus the present results provide that the microfluidic device of the pulmonary acinus are a promising tool for quantitative investigations of acinar flows by studying detailed flow patterns in a model featuring five generations of expanding and contracting alveolated ducts. Despite the simplicity and limitations of the microfluidic acinar network, our model reproduces essential flow properties of the acinus, providing for the first time experimental hydrodynamic evidence supporting the existence of a range of complex recirculating alveolar flows along the acinar tree, with a gradual cross-over to radial-like patterns in distal alveolated generations. In addition, the model is versatile in the sense that it allows a precise control of inlet velocities and wall strains that can in principle be adjusted to represent different regions of the acinus and different breathing conditions. Finally, our microfluidic device represents an attractive alternative to scaled-up models of acinar flows since it features several generations of moving-wall acinar ducts at a realistic anatomical scale. This latter aspect renders our microfluidic approach particularly amenable to studies of particle transport in the acinus where scaled-up models fail to capture hydrodynamic similarity for both flows and particles.

Example 5

Artificial Breathing

A study has been conducted using polystyrene red fluorescent particles (Fluoromax, Thermo Scientific) with particle diameters of 0.1, 0.5 and 1 μm and 1 h exposure time during which the microfluidic prototype was artificially breathing with a quiet physiologically-real breathing cycle. After the exposure assay, the particles were imaged using fluorescent microscopy and the location of particles deposited on the bottom of the channels was determined using image analysis. FIG. 9 shows particle location and corresponding density maps for the three different particle sizes, illustrating the feasibility and applicability of using the present technology and devices for accurately assessing in-vitro deposition patterns of inhaled aerosols.

Example 6

Facilitating Exposure to Air-Borne Particles without the Use of a Large Exposure Chamber The microfluidic acinar device (also referred to as microfluidic assembly) was shown to facilitate exposure to airborne particles without the use of a large exposure chamber. The chamber housing the microfluidic device is a chamber wherein the microfluidic device is inserted to the device featuring an inlet and an outlet through which a steady stream of aerosol is driven. From the "in-device chamber" the aerosol was sucked at a constant velocity using a syringe pump through an auxiliary channel which reached close to the aerosol inlet of the acinar tree. The aerosol was inhaled into the tree as a result of actuation of the device walls. The use of an in-device chamber and an auxiliary channel ensures that the particles are convected close enough to the opening of the acinar tree to allow a significant amount of particles to enter the device.

What is claimed is:

1. A microfluidic device comprising at least 3 chambers, a chamber inlet, at least 2 dichotomously branching generations of channels, and a channel inlet, said channels and said chambers are separated and defined by deformable walls, wherein each wall is lined with at least one cavity, said cavity is fluidly connected to said channel.

2. The device of claim 1, further comprising a channel outlet.

3. The device of claim 1, where said cavity is cylindrical.

4. The device of claim 1, where said cavity is rectangular.

5. The device of claim 1, where said cavity is polyhedral.

6. The device of claim 1, where said deformable walls are inflatable.

7. The device of claim 1, where said chamber is filled with a fluid.

8. The device of claim 3, where said fluid is water, an aqueous solution or air.

9. The device of claim 1, further comprising a pump coupled to said chamber inlet.

10. The device of claim 1, wherein said channels range from 200 to 800 micrometers wide.

11. The device of claim 1, wherein said channels are 300 micrometers to 1.5 millimeters long.

12. The device of claim 3, wherein said cylindrical cavity has a radius of 50 to 150 micrometers.

13. The device of claim 4, wherein said rectangular cavity has a side size of 50 to 150 micrometers.

14. The device of claim 5, wherein said polyhedral cavity has a width of 100 to 300 micrometers.

15. The device of claim 1, wherein said walls are 15 to 80 micrometers thick.

16. The device of claim 1, wherein said walls are 40 to 800 micrometers high.

17. The device of claim 1, the aspect ratio of said channels' height to width is 0.5 to 8.

18. The device of claim 1, wherein the distance between a channel edge and the center of said cylindrical cavity opening (E) is 20 to 140 micrometers.

19. The device of claim 1, wherein said cylindrical cavity opening has a half-angle of 20° to 80°.

20. The device of claim 1, wherein said deformable walls comprise a polymeric organosilicon compound.

* * * * *